United States Patent
Avinash et al.

(10) Patent No.: US 7,389,136 B2
(45) Date of Patent: *Jun. 17, 2008

(54) METHOD AND SYSTEM USING A NON-ELECTRICAL SENSOR FOR GATING

(75) Inventors: Gopal B. Avinash, New Berlin, WI (US); Prathyusha K. Salla, Waukesha, WI (US); Cherik Bulkes, Sussex, WI (US); TinSu Pan, Brookfield, WI (US); Bernice E. Hoppel, Delafield, WI (US); Scott Thomas Mansell, Waterford, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 926 days.

This patent is subject to a terminal disclaimer.

(21) Appl. No.: 10/065,960

(22) Filed: Dec. 4, 2002

(65) Prior Publication Data

US 2004/0111025 A1    Jun. 10, 2004

(51) Int. Cl.
*A61B 5/05* (2006.01)
(52) U.S. Cl. .................................... 600/413
(58) Field of Classification Search ........ 600/407–482; 128/898
See application file for complete search history.

(56) References Cited

U.S. PATENT DOCUMENTS

| | | | |
|---|---|---|---|
| 4,712,560 A | 12/1987 | Schaefer et al. | 128/653 |
| 5,797,395 A | 8/1998 | Martin | 128/673 |
| 5,853,005 A * | 12/1998 | Scanlon | 600/459 |
| 5,987,983 A | 11/1999 | Ariav et al. | 73/488 |
| 5,997,883 A | 12/1999 | Epstein et al. | 424/306 |
| 6,024,705 A * | 2/2000 | Schlager et al. | 600/508 |
| 6,070,097 A | 5/2000 | Kreger et al. | 600/521 |
| 6,076,005 A * | 6/2000 | Sontag et al. | 600/413 |
| 6,144,874 A | 11/2000 | Du | 600/413 |
| 6,144,880 A * | 11/2000 | Ding et al. | 607/23 |
| 6,149,602 A * | 11/2000 | Arcelus | 600/523 |
| 6,243,437 B1 | 6/2001 | Hu et al. | 378/8 |
| 6,275,560 B1 | 8/2001 | Blake et al. | 378/8 |
| 6,434,215 B1 | 8/2002 | Cesmeli | 378/8 |
| 6,771,999 B2 * | 8/2004 | Salla et al. | 600/413 |
| 2003/0036693 A1 | 2/2003 | Avinash et al. | 600/413 |

* cited by examiner

*Primary Examiner*—Eric F. Winakur
*Assistant Examiner*—Michael Rozanski
(74) *Attorney, Agent, or Firm*—Cantor Colburn LLP

(57) ABSTRACT

A method and system of gating for a medical imaging system includes utilizing a non-electrical sensor to acquire information for gating. A sensor assembly usable in the method and system of gating may include a non-electrical sensor coupled to one side of a patient-sensor interface, the other side adapted for securing to a patient.

28 Claims, 5 Drawing Sheets

METHOD AND SYSTEM USING A NON-ELECTRICAL SENSOR FOR GATING

BACKGROUND OF THE INVENTION

This invention relates to gating for imaging systems, and more particularly, this invention relates to a system and method for obtaining cardiac, peripheral pulse, and respiratory gating signals for improving the timing of image acquisition.

In the medical field, imaging systems are often used to obtain internal physiological information of a subject. For example, a medical imaging system may be used to obtain images of the bone structure, the brain, the heart, the lungs, and various other features of a subject. Medical imaging systems include magnetic resonance imaging (MRI) systems, computed tomography (CT) systems, x-ray systems, ultrasound systems, and various other imaging modalities.

In many applications, it is often desirable to obtain an image at a particular point in a variable cycle, such as a peak of the variable cycle, to analyze behavior at that peak. Gating is an option for characterizing different attributes of an organ for imaging. The most common techniques of gating including cardiac, respiratory, and peripheral pulse gating and these types of gating have uses in numerous medical applications across diagnostic modalities including CT, MR, X-Ray, Ultrasound, and PET-CT.

Cardiac gating, as an example, is an essential component of cardiac imaging while using imaging modalities such as CT, Magnetic resonance (MR) to minimize motion related artifacts. Current method involves using electrocardiogram (EKG) for determining gating pulse. Essentially, the R-wave of the EKG is used for this purpose. FIG. 1 illustrates one cardiac cycle of an EKG signal waveform, including a systole condition, or period, and a diastole condition, or period, of the heart. The portions of the EKG signal labeled Q, R and S are referred to as the QRS complex, in which the R-feature, or R-wave, is the most prominent, highest amplitude, feature of the entire EKG signal. The cardiac cycle is typically defined as beginning with an R-wave and continuing until the occurrence of a next R-wave.

EKG gating selects times when a best image of the heart is available. An EKG machine is connected to a patient. A cardiac cycle period is determined, for example, as a time between R-peaks of the EKG. Using an R-peak as a reference and the determined cardiac cycle period, image acquisition during a scan is gated so that image data is acquired only during periods of a cardiac cycle for which the heart is nearly stationary. Thus, only an electrical system has been utilized for gating medical imaging.

BRIEF SUMMARY OF THE INVENTION

The above discussed and other drawbacks and deficiencies are overcome or alleviated by a method of gating for a medical imaging system including selecting a non-electrical sensor from a group consisting of an acceleration sensor and a force sensor and utilizing the non-electrical sensor to acquire information for gating.

In another embodiment, a method of gating for a medical imaging system includes selecting a non-electrical sensor from a group consisting of an accelerometer, force sensor, ultrasonic sensor, strain gage, photodiode, and pressure sensor and utilizing the non-electrical sensor to acquire information for cardiac gating.

In another embodiment, a method of gating for a medical imaging system includes selecting a non-electrical sensor from a group consisting of an accelerometer and a force sensor and utilizing the non-electrical sensor to acquire information for respiratory gating.

In another embodiment, a method of gating for a medical imaging system includes selecting a non-electrical sensor from a group consisting of an accelerometer, force sensor, ultrasonic sensor, strain gage, photodiode, interferometer, laser, and pressure sensor and utilizing the non-electrical sensor to acquire information for peripheral pulse gating.

In another embodiment, a method of using a sensor for gating including providing a non-electrical sensor, providing a fluid filled transmission tube having a first end and a second end, attaching the first end of the fluid filled transmission tube to the patient, and attaching the second end of the fluid filled transmission tube to a sensor.

In another embodiment, a sensor assembly includes a non-electrical sensor is adapted for resting on a vibrating surface, a patient-sensor interface having a first end and a second end, the first end adapted for securing to a patient, the second end coupled to the sensor.

The above discussed and other features and advantages of the present invention will be appreciated and understood by those skilled in the art from the following detailed description and drawings.

DETAILED DESCRIPTION OF THE INVENTION

Figure 1:
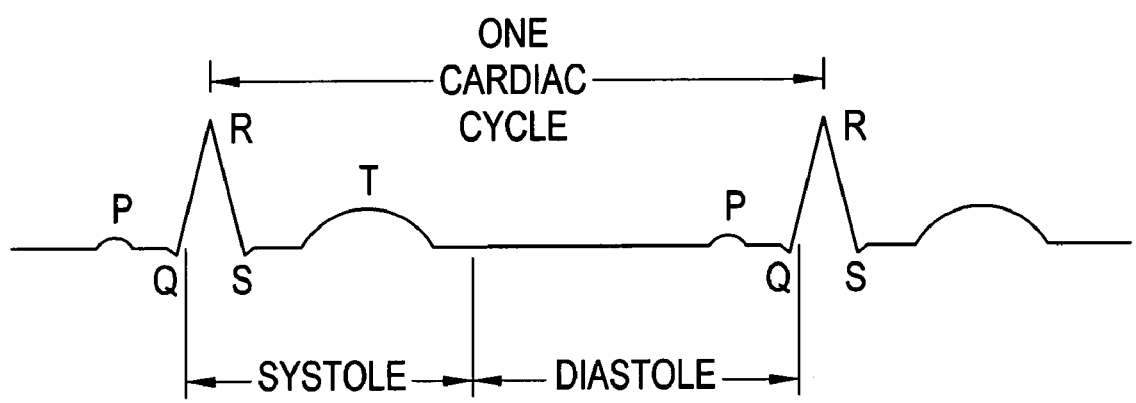
FIG. 1 shows a prior art EKG signal waveform used in known imaging systems.
Figure 2:
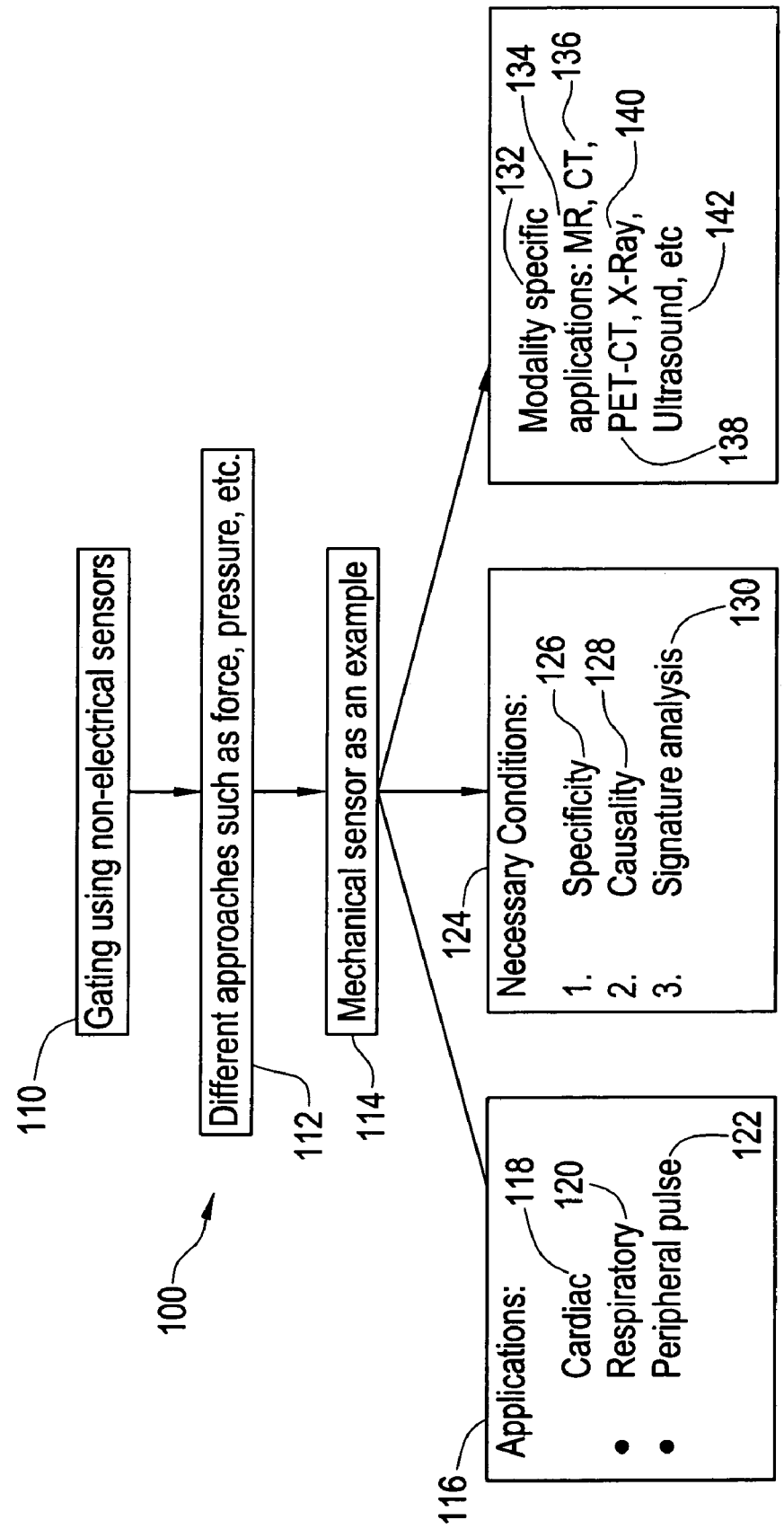
FIG. 2 shows an organizational chart for the method of using a non-electrical sensor for gating.

FIG. 2 shows an organizational breakdown of the method 100 for using a non-electrical sensor for gating 110. The non-electrical sensor approach is an alternative means to gating and can be an adjunct to the current gating standard (EKG). By non-electrical sensor, it should be understood that the sensor is capable of detecting some type of physical, non-electrical occurrence in the body. As indicated in 112, various types of physical, non-electrical phenomena that may be utilized include force, pressure, acceleration, optical, ultrasound, etc. As will be further described below, a mechanical sensor 114 is one example of a non-electrical sensor that may be used for gating in the method 100.

As shown in 116, the various applications that may employ gating using a non-electrical sensor include cardiac 118, respiratory 120, and peripheral pulse 122. It should be noted that other applications, such as, for example, non-medical applications, may also be gated using the method 100.

As shown in 124, for a method 100 based on mechanical motion to be applicable for gating for a particular application 116, the following three conditions 124 should apply: 1) specificity 126: as an example, for a cardiac application 118, the gating signal must be derived from an event that is cardiac in origin; 2) causality 128: as an example, for a cardiac application 118, the gating signal needs to occur just before the cardiac displacement occurs (i.e., need to have capability to "look forward in time"); and, 3) signature analysis 130: the gating signal must be reliably obtained using a signature analysis approach.

The last leg in the breakdown of the method 100 refers to the modality specific applications 132 which may incorporate gating 110 using a non-electrical sensor. Such modalities include, but are not limited to, MR 134, CT 136, PET-CT 138, X-ray 140, Ultrasound 142, etc.

For exemplary purposes, a mechanical sensor will be described as one possible embodiment of the non-electrical sensor, although other types of non-electrical sensors are also usable in this method. Also for exemplary purposes, an accelerometer will be described as one possible embodiment of a mechanical sensor, although other types of mechanical sensors are also usable in this method.

Figure 3:
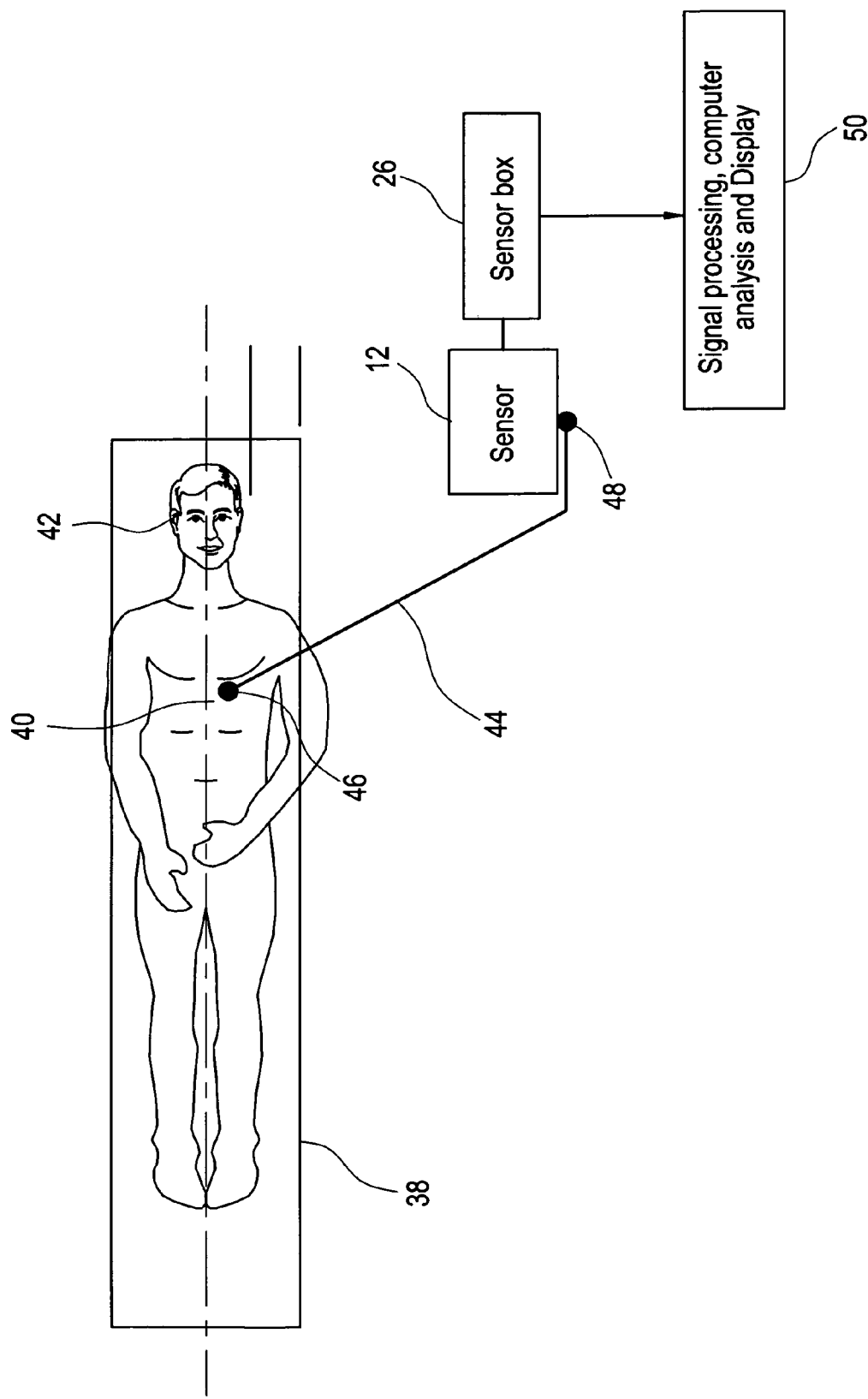
FIG. 3 shows a diagram of a sensor assembly arranged relative to a patient.

In order to improve specificity, a sensor assembly, such as an accelerometer or any of the other non-electrical sensors described above, may be placed directly on the chest wall 40 in front of the heart of a patient 42 who is preferably supine on a table 38 as shown in FIG. 3. Alternatively, if the sensor 12 is interfering with imaging, the sensor 12 may be removed from the imaging field of view through the use of a patient-sensor interface 44 such as but not limited to fluid filled, non metallic, non conducting tube. The interface 44 may have a flat end 46, which is stuck, adhered, or otherwise secured to the patient 42, and the other end 48 may be coupled to the sensor 12. With this arrangement, the vibrations specific to the heart are conducted away to the sensor 12, which is located outside the imaging field of view. The cardiac vibrations from the patient are transferred using the patient-sensor interface 44 to the sensor 12. If the sensor 12 is an accelerometer, then acceleration is recorded by the sensor box 26 and sent to signal processing, computer analysis and display 50. Alternate methods for removing the sensor 12 away from the imaging field of view are also usable within this method, as well as placing the sensor 12 directly on the chest 40 of the patient 42 when such a placement does not interfere with imaging.

When a non-electrical sensor such as an accelerometer is placed in contact with a moving body, for instance, the front chest wall 40 as shown in FIG. 3, movement of the front chest wall 40 representing the mechanical motion of the heart is detected. Other non-electrical sensors including force sensor, ultrasonic sensor, strain gage, photodiode and pressure sensor may be represented by sensor 12 where patient-sensor interface 44 may or may not be utilized to couple or orientate the sensor 12 relative to the physical occurrence of the patient to be sensed.

Figure 4:
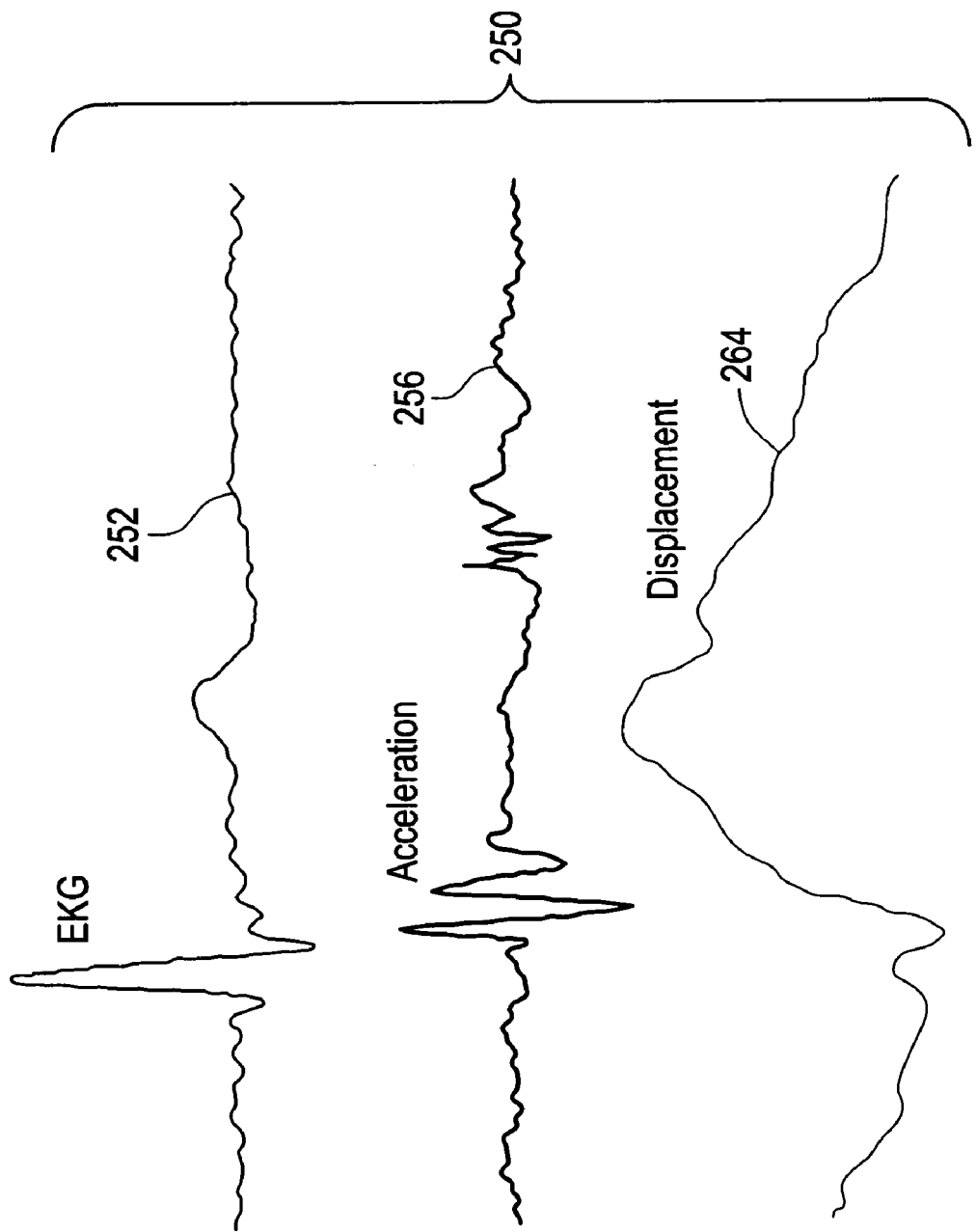
FIG. 4 shows a diagram of an EKG waveform, an acceleration signal, and a displacement waveform.
Figure 5:
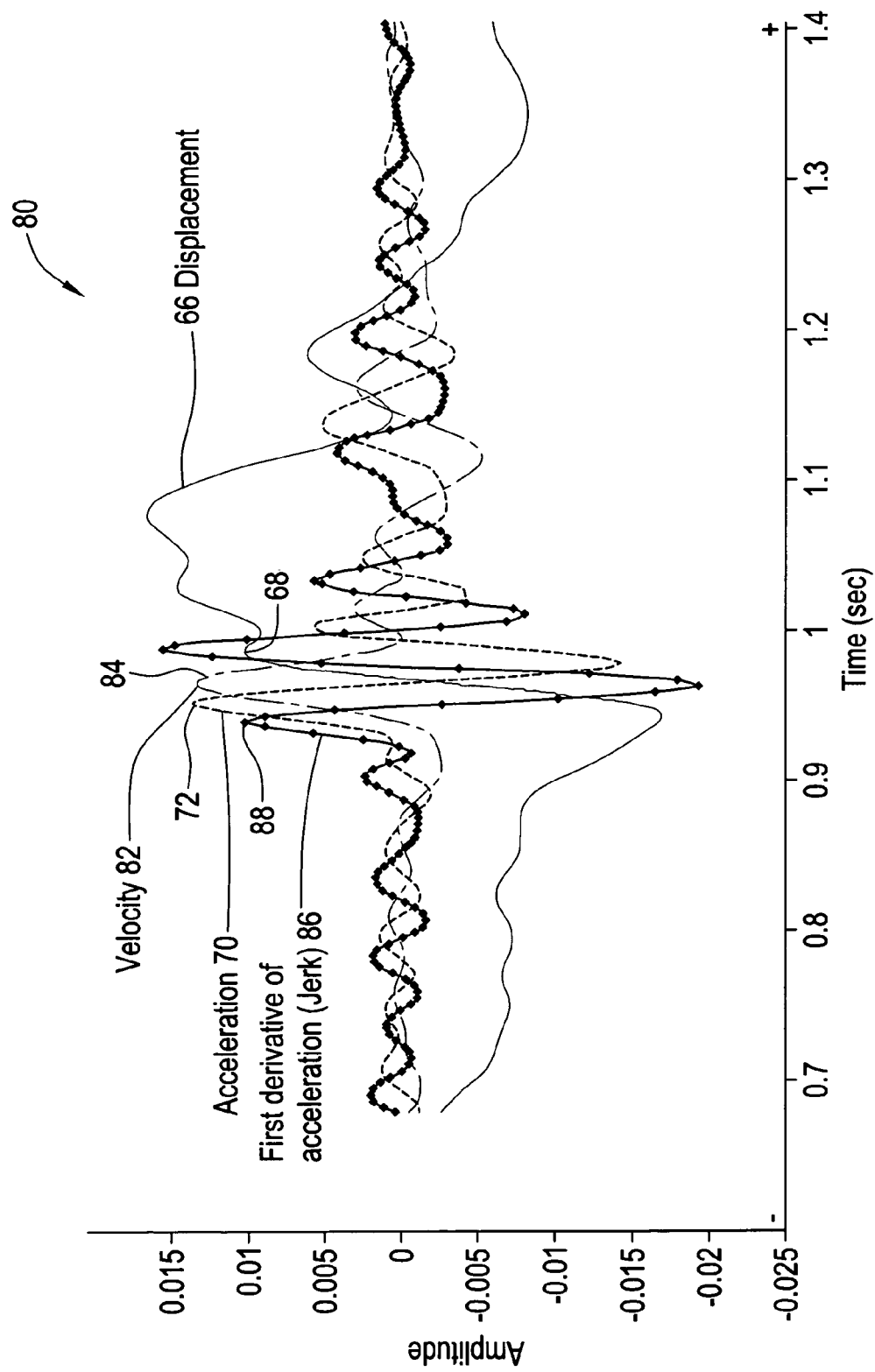
FIG. 5 shows a graph plotting displacement, velocity, acceleration, and first derivative of acceleration waveforms.

Turning to FIG. 4, EKG 252, acceleration 256, and displacement waveforms 264, shown together at 250, are shown plotted on the same timeline. It should be understood that information extracted in one mode may be used to computationally derive information in another mode without having to use multiple sensors. Thus, information may either be derived computationally or may be acquired directly from a sensor. Generally, an operator would most likely employ the computational method only if information could not feasibly or desirably be obtained using a direct method. As an example, the blood pressure waveform, or displacement signal 264 may be computationally derived from the acceleration waveform 256 by integrating the signal 256 twice over a given time interval and getting rid of the drift in the signal. Alternatively, as another example, the acceleration waveform 256 may be derived from the pressure waveform 264 by a second order derivative operation. The blood velocity factor (not shown) can be derived in the same way be either integrating the acceleration signal 256 over a given interval of time or by taking a first order derivative of the pressure waveform 264 and vice versa. Thus, information may either be derived computationally or may be acquired directly from a sensor. Generally, an operator would most likely employ the computational method only if information could not feasibly or desirably be obtained using a direct method. Causality of the signal can be addressed by differentiating the acquired signal N (N greater or equal to 1) times. As the higher derivatives are taken, the time point of an event shifts to an earlier time as shown in FIG. 5. FIG. 5 shows displacement, velocity, acceleration and first derivative of acceleration (jerk) waveforms plotted on the same graph 80 of amplitude vs. time. The graph 80 illustrates the salient-peak shifting to a prior time, thus providing a "looking forward in time" concept. That is, displacement waveform 66 has salient peak 68 which occurs at a later time than salient peak 84 for velocity waveform 82. Correspondingly, salient peak 84 for velocity waveform occurs at a later time than salient peak 72 for acceleration waveform 70, which in turn occurs at a later time than salient peak 88 for the first derivative of acceleration (jerk) waveform 86. It should be understood that the acquired signals are exemplary only, and that reported signals from different patients would most likely vary along the timeline. What is consistent, however, is that each consecutive derivative of the displacement waveform 66 occurs at a time prior to the prior derivative. A sensor bandwidth of 125 Hz or above may be required for obtaining jerk information from the waveforms. The bandwidth requirements go up if higher derivatives of jerk need to be computed.

Signature analysis 130 may be modeled using the mechanical data from a population. The variations due to demographics and pathologies can be characterized and evaluated. With the training set in hand, standard pattern recognition techniques can be used to extract the gating signal from the data, such as further described in U.S. patent application Ser. No. 10/065,961, filed concurrently herewith and incorporated by reference in its entirety.

One method of obtaining cardiac information may include differentiating an acceleration signal from an accelerometer to obtain jerk or any other higher order derivative. The derived signal may then be subject to signature analysis as further described in U.S. patent application Ser. No. 10/065, 961, filed concurrently herewith and incorporated by reference in its entirety, to extract the salient peaks. The location of salient peaks would in turn serve as the trigger points for a gating signal.

On the other hand, the preferred method to obtain respiratory information is to use a non-electrical sensor at a location such as the chest or stomach based on his/her breathing pattern that gives predominantly respiratory signal. If this is not possible, another method of obtaining respiratory information may include integrating an acceleration signal twice, assuming the displacement signal is not desirably obtainable. The resultant signal may be band pass filtered to remove very low frequencies that cause drift in the signal and high frequencies corresponding to cardiac motion. The resultant signal may then be analyzed for salient peaks and the knowledge about their location may be used for obtaining respiratory trigger points. On the other hand, one method of obtaining peripheral pulse information may include placing an accelerometer on an artery (e.g., the radial artery on a person's wrist) and extracting an acceleration signal. The time delay for any information to be transmitted from the heart to the peripheral pulse may be accounted for while characterizing the signal.

It should be understood that the above examples of obtaining cardiac, respiratory, and peripheral pulse information are exemplary only as the accelerometer is only one of many possible types of non-electrical sensors. It should also be understood that alternate non-electrical sensors may be employed with any of the described methods to acquire alternate signal patterns which may be directly applicable or may require integrating one or more times or obtaining one or more derivatives for computationally deriving the required information.

Thus, it has been described how gating is made possible with a non-electrical sensor thereby enabling new applications not previously possible. The methods disclosed herein serve as alternative methods for cardiac, respiratory, and peripheral pulse gating. Specificity, causality, and signature analysis are dealt with for each of cardiac, peripheral pulse, and respiratory physiological data. The "looking forward in time" concept has also been described, which does not use the traditional prediction techniques but rather involves analyzing derivatives of waveforms. Furthermore, the signals described above make signature analysis possible to obtain reliable gating signals. This system and method is applicable for CT, MR, X-Ray, and Ultrasound products for cardiac, respiratory and peripheral pulse gating.

It should be noted that all of the methods described above may be employed within an imaging system or within a signal processor associated with a computer and display such as shown by item 50 in FIG. 3, and in particular, may be stored within a memory processed by a processing circuit in the processor. It is further within the scope of this invention that the disclosed methods may be embodied in the form of any computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method of gating for a medical imaging system, the method comprising:
   selecting a non-electrical sensor, the non-electrical sensor being an acceleration sensor;
   utilizing the non-electrical sensor to acquire information for gating;
   determining a gating signal relative to and prior to a predisposed displacement of a body part of a patient by determining a feature of the acquired information; and
   gating using the gating signal.

2. The method of claim 1 wherein the gating comprises gating within a magnetic resonance imaging system.

3. The method of claim 1 wherein the gating comprises gating within a computed tomography imaging system.

4. The method of claim 1 wherein the gating comprises gating within a PET-CT imaging system.

5. The method of claim 1 wherein the gating comprises gating within an X-ray imaging system.

6. The method of claim 1 wherein the gating comprises gating within an ultrasound imaging system.

7. The method of claim 1 further comprising obtaining the gating signal using signature analysis.

8. The method of claim 7 wherein using signature analysis includes providing a training set within a database and employing a pattern recognition technique to extract a gating signal.

9. The method of claim 1 further comprising utilizing the non-electrical sensor to acquire information for respiratory gating.

10. The method of claim 9 further comprising
    obtaining an acceleration waveform with the accelerometer;
    integrating the acceleration signal twice to obtain a resultant signal;
    band pass filtering the resultant signal to remove frequencies that cause drift in the resultant signal and frequencies corresponding to cardiac motion to obtain a filtered signal;
    analyzing the filtered signal for salient peaks; and
    obtaining a trigger point for respiratory gating.

11. The method of claim 1 wherein:
    the determining comprises:
       calculating a first derivative of an acceleration waveform to obtain a jerk waveform; and
       determining a salient-peak of the jerk waveform; and
    the gating comprises utilizing the salient-peak as a trigger point.

12. A method of gating for a medical imaging system, the method comprising:
    selecting a non-electrical accelerometer;
    utilizing the non-electrical accelerometer to acquire information for cardiac gating;
    sensing cardiac vibrations with the accelerometer and acquiring an acceleration waveform with the accelerometer;
    calculating a first derivative of the acceleration waveform to obtain a jerk waveform;
    determining a salient-peak of the jerk waveform; and
    gating using the salient-peak as a trigger point.

13. The method of claim 12 further comprising obtaining the gating signal using signature analysis.

14. The method of claim 13 wherein using signature analysis includes providing a training set within a database and employing a pattern recognition technique to extract a gating signal.

15. A method of gating for a medical imaging system, the method comprising:
  selecting a non-electrical sensor, the non-electrical sensor being a force sensor;
  utilizing the non-electrical sensor to acquire information for gating;
  determining a gating signal relative to and prior to a predisposed displacement of a body part of a patient by determining a feature of the acquired information; and
  gating using the gating signal.

16. The method of claim 15 further comprising utilizing the non-electrical sensor to acquire information for respiratory gating.

17. The method of claim 15 wherein:
  the determining comprises:
    calculating a first derivative of an acceleration waveform to obtain a jerk waveform; and
    determining a salient-peak of the jerk waveform, and utilizing the salient-peak as a trigger point for the gating; and
  the gating comprises utilizing the salient-peak as a trigger point.

18. A method of gating for a medical imaging system, the method comprising:
  selecting a non-electrical accelerometer;
  arranging the accelerometer on a wrist of a patient;
  utilizing the non-electrical accelerometer to acquire information for peripheral pulse gating;
  determining a gating signal relative to and prior to a predisposed displacement of a body part of a patient by determining a feature of the acquired information; and
  gating using the gating signal.

19. The method of claim 18 further comprising
  obtaining an acceleration waveform from the accelerometer;
  calculating a time delay for information being transmitted from a heart of the patient to a peripheral pulse; and
  characterizing the signal.

20. The method of claim 18 wherein:
  the determining comprises:
    calculating a first derivative of an acceleration waveform to obtain a jerk waveform; and
    determining a salient-peak of the jerk waveform, and utilizing the salient-peak as a trigger point for the gating; and
  the gating comprises utilizing the salient-peak as a trigger point.

21. A method of using a sensor for gating, the method comprising:
  providing a non-electrical accelerometer;
  providing a fluid filled transmission tube having a first end and a second end;
  attaching the first end of the fluid filled transmission tube to a chest wall of a patient adjacent a heart of the patient;
  attaching a second end of the fluid filled transmission tube to the sensor;
  utilizing the non-electrical accelerometer to acquire information for gating;
  determining a gating signal relative to and prior to a predisposed displacement of a body part of a patient by determining a feature of the acquired information; and
  gating using the gating signal.

22. The method of claim 21 further comprising placing the sensor out of a field of view during an imaging process.

23. The method of claim 21 further comprising connecting the sensor to a sensor box via an electrical connection for recording information acquired by the sensor.

24. The method of claim 23 further comprising sending information from the sensor box to a signal processing and computer analysis station.

25. The method of claim 21 wherein providing a non-electrical sensor comprises providing a sensor having a bandwidth of at least 125 Hz.

26. The method of claim 21 wherein:
  the determining comprises:
    calculating a first derivative of an acceleration waveform to obtain a jerk waveform; and
    determining a salient-peak of the jerk waveform, and utilizing the salient-peak as a trigger point for the gating; and
  the gating comprises utilizing the salient-peak as a trigger point.

27. A method of using a sensor for gating, the method comprising:
  providing a non-electrical accelerometer;
  providing a fluid filled transmission tube having a first end and a second end;
  attaching the first end of the fluid filled transmission tube to a wrist of a patient adjacent a radial artery of the patient;
  attaching a second end of the fluid filled transmission tube to the sensor;
  utilizing the non-electrical accelerometer to acquire information for gating;
  determining a gating signal relative to and prior to a predisposed displacement of a body part of a patient by determining a feature of the acquired information; and
  gating using the gating signal.

28. The method of claim 27 wherein:
  the determining comprises:
    calculating a first derivative of an acceleration waveform to obtain a jerk waveform; and
    determining a salient-peak of the jerk waveform, and utilizing the salient-peak as a trigger point for the gating; and
  the gating comprises utilizing the salient-peak as a trigger point.

* * * * *